US00PP08799P

United States Patent [19]

Mantel

[11] Patent Number: Plant 8,799

[45] Date of Patent: Jun. 21, 1994

[54] LILY PLANT LILIUM 'SCARLET DWARF'

[75] Inventor: Homme Mantel, Sandy, Oreg.

[73] Assignee: Mt Hood Lilies, Inc., Sandy, Oreg.

[21] Appl. No.: 100,707

[22] Filed: Jul. 30, 1993

[51] Int. Cl.[5] ..... A01H 5/00

[52] U.S. Cl. ..... Plt./87.4

[58] Field of Search ..... Plt. 87.4

*Primary Examiner*—James R. Feyrer

[57] ABSTRACT

A new variety of hybrid lily plant bearing large upright-facing flowers of excellent form and long persistence. The new hybrid is particularly characterized by a compact inflorescence of upfacing flowers of vibrant unspotted scarlet red color and with lightly ruffled tepal margins, and with buds also a deep scarlet red color. This combination is completely new in the Asiatic hybrid divisions of lilies suited to forcing and to mass commercial cultivation. The variety is highly resistant to fusarium disease and shows tolerance of virus. The bulbs may be precooled and forced into flower under glass out of season. The clone is vigorous and is a good grower and propagator.

1 Drawing Sheet

BACKGROUND OF THE INVENTION

My new variety of lily plant originated as a seedling, which first flowered in 't Zand, Netherlands in 1986. The breeding efforts had as their objective the production of Asiatic hybrid lilies with upfacing, vibrant red flowers in a compact inflorescence, suited to forcing into flower out of season, heretofore unknown in the lily breeding art. I achieved the desired objective by intercrossing Lilium 'Charisma' (U.S. Plant Pat. No. 4,180) with Lilium 'Red Carpet' (unpatented). The flowers of my new lily are characterized by an upright orientation, large size, and a vibrant red color; and they are borne on a compact inflorescence. The clone possesses unusually strong, stout stems. In addition, it possesses to a high degree desirable characteristics of hybrid vigor. The clone is a good grower and propagator, as observed at 't Zand, Netherlands.

My new variety of lily plant has been asexually reproduced by me and under my direction at 't Zand, Netherlands. Successive generations produced by natural propagation from bulblets, by bulb scale propagation, and by tissue culturing from bulb scale explants have demonstrated that the novel and distinctive characteristics of my new variety are fixed and hold true under asexual propagation from generation to generation.

The most closely related plant known to myself is a sibling plant from the same cross named 'Red Dwarf'. This sibling is the subject of a copending application. While 'Scarlet Dwarf' and 'Red Dwarf' are similar in size, plant confirmation and flower characteristics, they are easily distinguished by the fact that the ovaries of 'Scarlet Dwarf' are much more conspicuous, being near straw color even when grown under very cool or intensely illuminated conditions, while those of 'Red Dwarf' are inconspicuous and nearly the red color of the tepals. Moreover, both the inner and outer tepals of 'Scarlet Dwarf' are slightly ruffled by marginal undulations, while such undulations are virtually confined to the inner tepals of 'Red Dwarf' and appear only on flowers that have been open for several days. The tepals of 'Scarlet Dwarf' are slightly stiffer, preventing them from reflexing to the same degree as those of 'Red Dwarf'. The flowers of 'Red Dwarf' are noticeably flatter than those of 'Scarlet Dwarf'.

DESCRIPTION OF THE DRAWING

My new variety of lily plant is illustrated in the accompanying photographic drawing, which shows the open bloom in full color and illustrates the flower form, the tepal arrangement, and in particular the novel and distinctive upfacing, vibrant red flowers with lightly ruffled tepal margins, the upfacing buds with deep red coloration, and the compact, semi-umbellate inflorescence.

DESCRIPTION OF THE NEW VARIETY

The following is a detailed description of my new variety of Asiatic hybrid lily, with nomenclature according to the *International Lily Register* (Royal Horticultural Society of London, Second Edition, 1969), and with color designations according to The Colour Chart of The Royal Horticultural Society, published by the Society in 1966.

THE PLANT

Origin: Seedling.

Seed parent: Lilium 'Charisma'.

Pollen parent: Lilium 'Red Carpet'.

Commercial classification: Hybrid Lilium clone.

Horticultural classification: Division IA, Upright Asiatic hybrid lily, according to the Horticultural Classification of Lilies, Royal Horticultural Society of London.

Form: Single stem, erect and stately.

Height: 60 to 85 cm from bulbs 14 to 18 cm in circumference, provided their light levels are adequate; low light levels may cause "stretching".

Growth: Vigorous and upright.

Internode length: Normally close to 3–6 mm at mid-stem. Forcing of the bulbs under glass after prolonged cold storage may produce shorter than typical stems with internodes as short as 1–2 mm at mid-stem. Forcing of very densely planted bulbs under glass with low light levels may cause atypically stretched stems with elongated internodes of 7–8 mm at mid-stem.

Foliage quantity: Abundant.

Size of leaf: 8 to 12 cm long×1.5–2.5 cm wide.

Shape of leaf: Lanceolate (pointed).
Texture: Leathery and glossy.
Color: Medium green, lighter on lower side.
Bulb size: Any size, ranging to 25 cm circumference commercially.
Bulb color: White, with flushes of pink or yellow after exposure to light.

THE BUD

Form: Obtuse, ovoid, and long.
Size: 7 to 9 cm long and 8 to 12 cm in circumference just prior to opening.
Opening: Bud opens slowly, in response to morning light; this takes about one hour.
Color: R.H.S. CC red 44 C to red 53 C, slightly lighter at base and apex.
Peduncle: Averages 2 to 5 cm, but it may elongate if light levels are too low or if bulbs have been improperly stored prior to forcing. Color is deep green with a light plum overlay.

THE FLOWER

Blooming habit: Annually in midseason; flowers once and profusely.
Size: Flowers are large-sized, averaging 15 to 17 cm in diameter, reflexing at the tips on the second day to 14 to 16 cm in diameter. The tepals are broad: outer tepals are 1.75 to 2.5 cm wide at the center, and the inner tepals are 2.25 to 3 cm wide at the center.
Borne: In a single compact racemic inflorescence producing 4 to 8 flowers from a bulb 14 to 16 cm in circumference. The raceme is so shortened that it appears to be an umbel, with all pedicels emerging from a single point. The inflorescence from very large bulbs may show a second tier of buds above the first, however.
Shape: Flowers form an open bowl with pointed, lightly recurved tepal tips by the second day after opening. As flower ages, both inner and outer tepals become lightly ruffled.
Tepalage: Typical of genus Lilium, with 6 imbricated tepals.
Tepal color: R.H.S. CC red 44 D to red 53 B, depending upon growing temperatures and light levels. Tepals will be lighter, less magenta-red, and more orange-red when grown with low light levels and high temperatures.
Tepal spotting: Tepals are unspotted.
Tepal longevity: Tepals stay on stems about three weeks.
Pedicel length: Average 5 to 8 cm long.
Pedicel color: Dark green with very light plum overlay.
Pedicel form: Sturdy and somewhat ascending.
Color changes: Flowers become slightly less scarlet and more orange-scarlet as the flowers age. Low light levels and extreme heat may cause a decrease in anthocyanin levels, making the color less scarlet.
Appearance: Flower is shiny.
Nectaries: present on both inner and outer tepals, substantially typical of the Asiatic Hybrid class, occassionally showing specks of callous near the apex of nectary channels.
Disease resistance: The flower and plant are resistant to disease; in particular, they are resistant to Fusarium bulb rot and Botrytis blight.
Fragrance: None.
Lasting quality: The flower is long lasting.

THE REPRODUCTIVE ORGANS

Stamens: Arrangement typical of genus Lilium. Six stamens with soft red (R.H.S. CC red 53 D) filaments 8 to 10 cm long.
Pollen and anthers (dehisced): R.H.S. CC greyed orange 172 A to greyed red 178 C.
Pistil: One in number, 6 to 9 cm long, R.H.S. CC red 53 D.
Stigma: Small in size, R.H.S. CC greyed red 181 C.
Characteristics of ovary: Characteristic of genus Lilium but conspicuous due to their attractively contrasting color, R.H.S. yellow 8 C/D to R.H.S. greyed yellow 162 D, which is distinctive when taken with remaining characteristics.

THE FRUIT

Fertility: The fruit bears fertile seed.
Shape: Ovoid.
Color at maturity: Soft brown, sometimes overlaid with soft plum.

My new variety of Asiatic hybrid lily most nearly resembles 'Red Carpet,' but it has larger, broader-petalled flowers of greater substance and a deeper scarlet red color. Its tepal tips do not recurve sharply as do those of 'Red Carpet', and it does not have conspicuously clawed tepals, as does 'Red Carpet'. It has a deeper red bud color, its inflorescence is more compact, and its pedicels and flowers are more upfacing.

I claim:

1. A new and distinctive variety of Asiatic hybrid lily plant substantially as herein shown and described, characterized by its high resistance to disease; its tolerance of virus; its vigorous growth and rapid natural propagation; the excellence of its flower form, size, and substance; its versatility both as a garden plant and as a pot plant produced from pre-cooled bulbs forced under glass out of season; and in particular by its unique compact inflorescence of scarlet red upfacing buds and scarlet red flowers with lightly ruffled tepal margins, a combination unique among Asiatic hybrid lilies suited to forcing and to mass commercial cultivation.

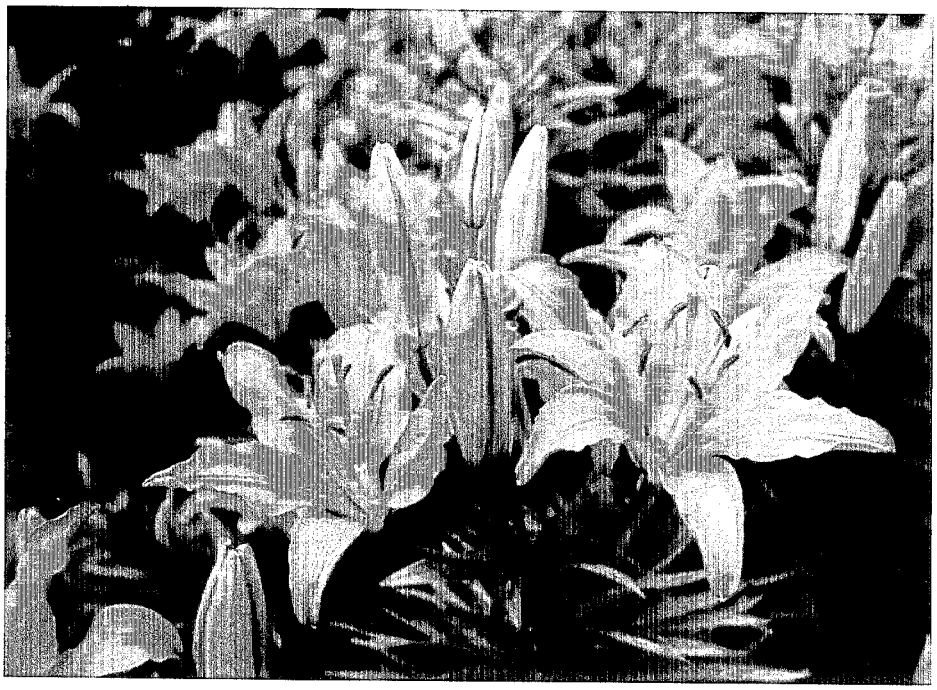

* * * * *